(12) United States Patent
Lee et al.

(10) Patent No.: US 8,067,376 B2
(45) Date of Patent: Nov. 29, 2011

(54) PHARMACEUTICAL COMPOSITIONS FOR TRANSDERMAL DELIVERY

(75) Inventors: Seung Kyou Lee, Yongin-si (KR); Sang Kyou Lee, Seoul (KR); Dong Ho Lee, Seoul (KR)

(73) Assignee: Forhumantech Co., Ltd., Hwaseong-Si, Gyeonggi-Do (KR)

( * ) Notice: Subject to any disclaimer, the term of this patent is extended or adjusted under 35 U.S.C. 154(b) by 757 days.

(21) Appl. No.: 11/667,185

(22) PCT Filed: Nov. 3, 2005

(86) PCT No.: PCT/KR2005/003698
§ 371 (c)(1),
(2), (4) Date: Apr. 15, 2008

(87) PCT Pub. No.: WO2006/049442
PCT Pub. Date: May 11, 2006

(65) Prior Publication Data
US 2008/0306075 A1    Dec. 11, 2008

(30) Foreign Application Priority Data
Nov. 3, 2004   (KR) .................. 10-2004-0088762

(51) Int. Cl.
*A61K 38/08*   (2006.01)
*A61K 39/385*  (2006.01)
*A61P 19/02*   (2006.01)
(52) U.S. Cl. .... 514/21.6; 530/328; 514/16.6; 424/193.1
(58) Field of Classification Search .................. None
See application file for complete search history.

(56) References Cited

U.S. PATENT DOCUMENTS

| 6,485,740 | B1 | 11/2002 | Tominaga et al. | |
| 2006/0293242 | A1* | 12/2006 | Temsamani et al. | 514/14 |

FOREIGN PATENT DOCUMENTS

| KR | 10-2004-0088568 | | 10/2004 |
| WO | 00/29427 A2 | | 5/2000 |
| WO | WO-00/64486 | * | 11/2000 |
| WO | 01/62297 A1 | | 8/2001 |
| WO | WO-03/059941 | * | 7/2003 |
| WO | WO-03059940 A1 | | 7/2003 |
| WO | WO-03059941 A1 | | 7/2003 |
| WO | WO-03/074551 | * | 9/2003 |
| WO | WO-2004013160 A2 | | 2/2004 |

OTHER PUBLICATIONS

Alvarez-Figueroa et al.; "Transdermal delivery of methotrexate: iontophoretic delivery from hydrogels and passive delivery from micromuolsions" In: International Journal of Pharmaceutics; 2001, 215(1-2); pp. 57-65.
Alvarez-Figueroa et al.; "*Passive and iontophoretic transdermal penetration of methotrexate*" In: International Journal of Pharmaceutics; 2001, 212(I); pp. 101-107.
Kabouridis, P.S., "Biological applications of protein transduction technology," TRENDS in Biotechnology, vol. 21, No. 11 (Nov. 2003).
Mait, J.C. et al., "Efficiency of Protein Transduction Is Cell Type-dependent and Is Enchanced by Destran Sulfate," The Journal of Biological Chemistry, vol. 377, pp. 30208-30218, 2002.
Shen, Wei-Chiang et al., "Poly (L-Lysine) and Poly (D-Lysine) Conjugates of Methotrexate: Different Inhibitory Effect on Drug Resistant Cells," Molecular Pharmacology, 16, pp. 614-622, 1979.
Official Action for Japanese Patent Application No. 2007-540252, issued Jan. 11, 2011.

* cited by examiner

*Primary Examiner* — Cecilia J Tsang
*Assistant Examiner* — Satyanarayana Gudibande
(74) *Attorney, Agent, or Firm* — Edwards Wildman Palmer LLP; Kongsik Kim

(57) ABSTRACT

The present invention relates to a pharmaceutical composition for transdermal administration comprising a conjugate of methotrexate and PTD (protein transduction domain). In accordance with the present invention, the methotrexate, which is widely used for the treatment of psoriasis, rheumatoid and inflammation, etc., can be delivered transdermally to a local part of a patient body, in order to minimize the side effect of the methotrexate.

5 Claims, 7 Drawing Sheets

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Biomolecule transduction motif

<400> SEQUENCE: 1

Tyr Ala Arg Val Arg Arg Arg Gly Pro Arg Arg
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Biomolecule transduction motif

<400> SEQUENCE: 2

Ala Lys Ala Ala Arg Gln Ala Ala Arg
 1               5
```

PHARMACEUTICAL COMPOSITIONS FOR TRANSDERMAL DELIVERY

CROSS-REFERENCES TO RELATED APPLICATIONS

This application is a U.S. national phase application, pursuant to 35 U.S.C. §371, of PCT international application Ser. No. PCT/KR2005/003698, filed Nov. 3, 2005, designating the United States and published in English on May 11, 2006 as publication WO 2006/049442 A1, which claims priority to Korean application 10-2004-0088762, filed Nov. 3, 2004. The entire contents of the aforementioned patent applications are incorporated herein by this reference.

TECHNICAL FIELD

The present invention relates to a novel pharmaceutical composition containing a conjugate of methotrexate and PTD (protein transduction domain).

BACKGROUND ART

In general, methotrexate is widely known to inhibit the metabolism of folic acid necessary for the synthesis of DNA in cells and the growth and division of cells. Specifically, methotrexate inhibits the enzymatic activity of dihydrofolate reductase (DHFR), which is one of the enzymes involved in folic acid metabolism. Thus, methotrexate is a drug applicable to various diseases by inhibiting cell proliferation, which is effective against autoimmune diseases, such as rheumatoid arthritis and psoriasis, and shows a very fast effect that alleviates the symptoms of the diseases within about 2 weeks after administration. However, methotrexate is difficult to use for a long period of time, because side effects that cause serious liver toxicity, gastrointestinal disorders and injuries of the kidneys and hematopoietic organs have been continuously reported. Also, it is formulated mainly for oral or injection administration, but the oral administration of methotrexate involves significant inconvenience, such as administering the active drug in a dosage of 2.5 mg at 12-hr intervals three times weekly. For this reason, there has been a continued need for the development of a novel method for drug delivery that can increase the drug delivery efficiency of methotrexate to reduce the dosage thereof so as to minimize the side effects and that can eliminate the inconvenience of injection and oral administration.

Meanwhile, PTD (protein transduction domain) is a low-molecular-weight peptide used for the penetration of a physiologically active molecule into host cells, and a first reported PTD is TAT found in the surface protein of the HIV virus in the year 1998. This TAT PTD was reported to effectively deliver large-size proteins having a molecular weight of more than 120 kDa into cells within a short time. Since then, several PTD proteins of different amino acid sequences having functions similar to TAT PTD have been found and research for novel drug development and DDS studies using these peptides has been suggested. Accordingly, leading countries in the medical and pharmaceutical fields have made many efforts to find novel PTD and develop novel drugs using the same. Also, the present inventors have performed studies to develop PTD, and as a result, developed novel PTD that shows a significantly higher effect than the prior reported PTDs in delivering macromolecules (e.g., proteins) into cells in vitro and in vivo (see PCT/KR2003/000121 and PCT/KR2003/000122).

Thus, the present inventors prepared a conjugate of PTD and methotrexate for the effective local delivery of methotrexate, and applied a novel pharmaceutical composition for transdermal delivery containing the conjugate on the skin and observed the results. As a result, we surprisingly found that methotrexate was delivered to lesion sites through the epidermis to show pharmacological effects, thereby completing the present invention.

TECHNICAL PROBLEM

It is an object of the present invention to provide a novel pharmaceutical composition containing a conjugate of methotrexate and PTD.

It is another object of the present invention to provide a method for locally administering methotrexate by transdermal delivery.

MODE FOR INVENTION

Figure 1:
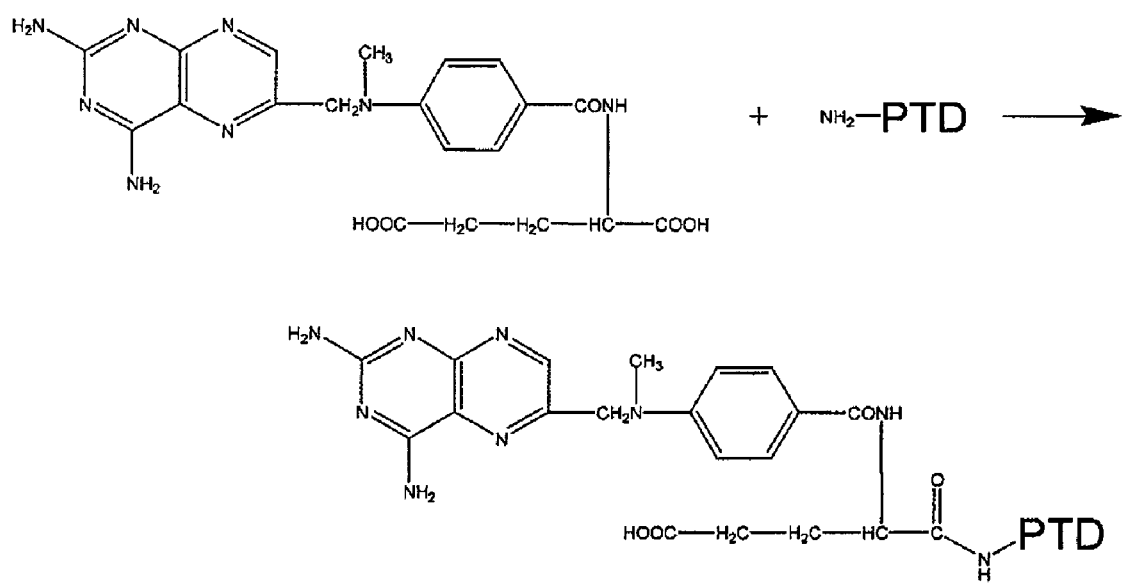
FIG. 1 shows the preparation of a conjugate (MTX-PTD) of MTX (methotrexate) and PTD (protein transduction domain) by a peptide bond.
Figure 2:
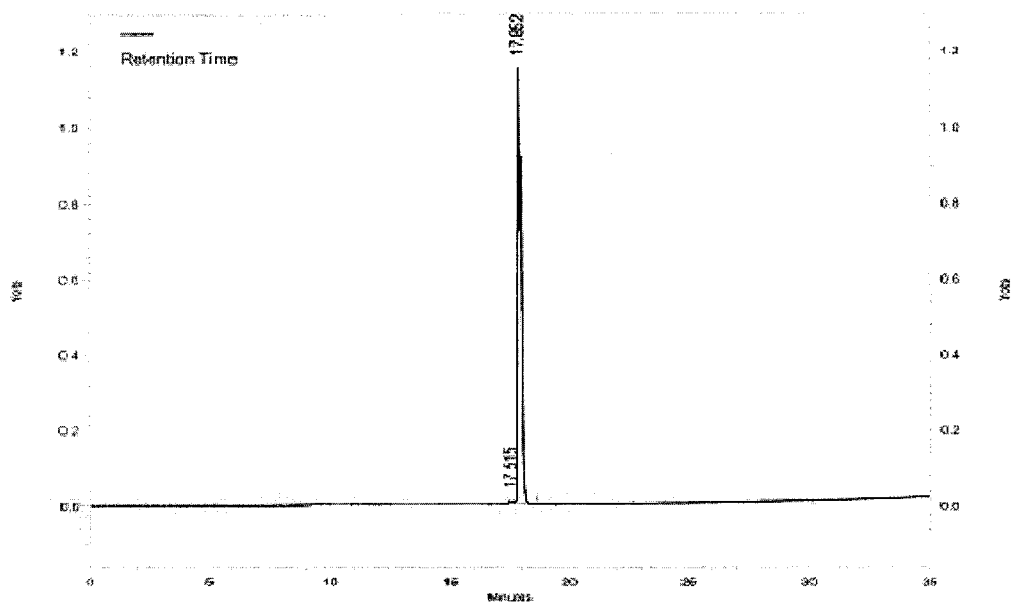
FIG. 2 shows HPLC analysis results for the MTX-PTD conjugate according to the present invention.
Figure 3:
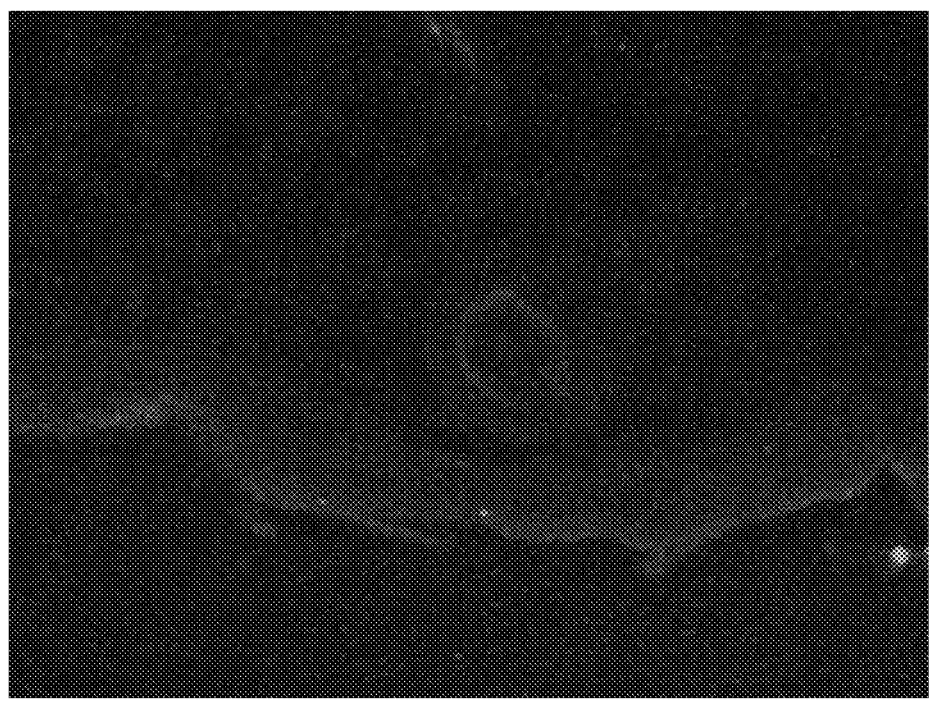
FIGS. 3 and 4 are confocal microphotographs showing the transdermal delivery of PTD used in the present invention.

To achieve the above objects, the present invention provides a conjugate of peptide PTD (protein transduction domain) and methotrexate (MTX) represented by Formula I. The inventive conjugate can be prepared by synthesizing PTD through a solid phase synthesis method and then linking the —COOH group of MTX to the N-terminal end of the synthesized PTD by a peptide bond (see FIG. 1).

[Formula I]

$$\text{Structure: pteridine-based MTX with CH}_3\text{-CH}_2\text{N-C}_6\text{H}_4\text{-CONH-CH(COOH)-CH}_2\text{-CH}_2\text{-COOH}$$

The MTX-PTD conjugate according to the present invention is easily delivered into cells in lesion sites through the epidermis by virtue of the intracellular penetration and delivery effects of PTD, and the conjugate delivered into the cells is decomposed by intracellular protease, and as a result, the separated MTX shows pharmacological effects. PTD used in the present invention has a very excellent property of delivering proteins, peptides, chemical compounds and the like into the body through the skin, eyeball or airway, and thus if it is provided as a conjugate with MTX, it can deliver MTX into local sites in the body through various administration routes. Also, MTX and PTD constituting the inventive conjugate can be linked to each other by various linkers, and particularly, by constructing a linker containing a region that is decomposed specifically by a certain enzyme, and it is possible to design the conjugate such that MTX can more effectively act in the desired local site. Linkers may vary depending on the purpose and direction of therapy, and in order to maximize effects in local sites, it is preferable to use linkers containing an —O— or —S—S— bond, which are decomposed easily in cells. For the purpose of systemic effects, it is preferable to introduce a spacer linker containing a peptide bond.

The PTD used in the present invention was developed by the present inventors and filed for patent. Namely, for use as PTD, each of the peptides set forth in SEQ ID NO: 1 and SEQ ID NO: 2 was prepared by a solid phase synthesis method. However, it can be understood that, according to the desired delivery sites and linkers used, other kinds of PTDs may also be used or peptides having at least 70% homology to the amino acid sequence of each of SEQ ID NO: 1 and SEQ ID NO: 2 may be used for the purpose of the present invention. The PTD used in the present invention consists preferably of 3-30 amino acids, at least 30% of which are arginines.

```
                                           (SEQ ID NO: 1)
    Tyr Ala Arg Val Arg Arg Arg Gly Pro Arg Arg (SEQ ID NO: 2)
    Ala Lys Ala Ala Arg Gln Ala Ala Arg
```

In the delivery of drugs through the skin, there are various limitations in view of the structural and physical properties of the skin. Particularly, the outermost horny layer of the skin comprises a compact structure resulting from the natural death of keratinocytes, the main cells of the skin, and inhibits the penetration of foreign material and the evaporation of water. Also, it is in an acidic range of around pH 5 due to sweat and various lipids. In order to allow PTD to penetrate this horny layer, it should have a low molecular weight of 1,000 or less and a lipophilic property.

The composition according to the present invention contains the MTX-PTD conjugate in an amount of 0.01-0.5% by weight based on the weight of the composition, together with a pharmaceutically acceptable carrier. Preferably, the inventive composition comprises 3-5% by weight of ethanol, 5-10% by weight of liquid paraffin, 30-40% by weight of Vaseline, 5-10% by weight of glycerin, 20-30% by weight of polyethylene glycol and 0.05-0.2% by weight of the MTX-PTD conjugate, all the amounts being based on the weight of the composition.

One embodiment of the present invention suggests measurement results for the intracellular penetration effects of PTD used in the present invention. FITC-conjugated PTD was measured for fluorescent intensity, and as a result, it was observed that PTD very effectively delivered FITC into cells.

In another embodiment of the present invention, a HeCaT cell line (obtained from Department of Dermatology, College of Medicine, Chungnam National University, Korea) was used to analyze the cell proliferation inhibitory effect of each of MTX alone, a MTX-PTD conjugate and a MTX-ACA-PTD conjugate. As a result, the MTX-ACA-PTD conjugate showed the highest inhibitory effect, followed by the MTX-PTD conjugate and the MTX alone in that order.

In still another embodiment of the present invention, the pharmacological effect of the MTX-ACA-PTD conjugate in arthritis animal models was measured. As a result, it was observed that a group (M3) administered transdermally with an ointment containing MTX-ACA-PTD showed substantially the same effect as those of a group (M2) injected intraperitoneally (I.P.) with MTX-ACA-PTD and a group (M1) injected intraperitoneally (I.P.) with MTX alone (see FIGS. 7, 8 and 9). Measurement results for IL-4, IL-6 and TNF-α levels and arthritis factor levels suggest that the MTX-ACA-PTD conjugate permeated the skin to effectively inhibit the activities of various inflammatory cells and immune cells.

As used herein, the term "immune cells" means T cells, B cells and the like.

As used herein, the term "inflammatory cells" means macrophages, eosinophils, neutorphils, basophils and the like.

The pharmaceutical composition according to the present invention can be formulated in various forms for oral or parenteral administration. Formulations for oral administration include, for example, tablets, pills, soft and hard capsules, liquids, suspensions, emulsions, syrups, granules and elixirs. These formulations may contain, in addition to the active ingredient, diluents (e.g., lactose, dextrose, sucrose, mannitol, sorbitol, cellulose and/or glycine), and lubricants, (e.g., silica, talc, stearic acid and a magnesium or calcium salt thereof, and/or polyethylene glycol). Tablets may also contain binders, such as magnesium aluminum silicate, starch paste, gelatin, tragacanth, methylcellulose, sodium carboxymethylcellulose and/or polyvinylpyrrolidone; if desired, disintegrants, such as starches, agar, alginic acid or its sodium salt, and azeotropic mixtures; and/or absorbents, colorants, flavors, and sweeteners.

The pharmaceutical composition containing the triptorelix-1 or its analogue as an active ingredient may be administered parenterally by subcutaneous, intravenous, intramuscular or intraperitoneal injection. For parenteral administration, the triptorelix-1 or its analogue may be mixed with a stabilizer or buffer in water to prepare a solution or suspension, which may then be provided as ampules or vials each containing a unit dosage form.

The inventive pharmaceutical composition may be sterilized and/or may contain adjuvants, such as preserving, stabilizing, wetting or emulsifying agents, solution promoters, salts for regulating the osmotic pressure and/or buffers. In addition, the composition may also contain other therapeutically effective substances. The composition can be formulated according to conventional mixing, granulating or coating methods.

In order to introduce the inventive peptide into cells, a fusion protein produced by fusing PTD (protein transduction domain) with the peptide may be used. As the protein transduction domain (PTD), any PTD known in the art may be used.

Triptorelix-1 or its analogue as an active ingredient may be administered to mammals, including human beings, in a dosage of 0.01-500 mg/kg of bodyweight, and preferably 0.1-50 mg/kg of bodyweight, one time a day or in divided dosages, by oral or parenteral routes. The dosage of the active ingredient can be suitably selected depending on the age, sex or disease severity of a patient.

Hereinafter, the present invention will be described in detail by examples. It is to be understood, however, that these examples are for illustrative purpose only and are not construed to limit the scope of the present invention.

EXAMPLES

Example 1

Synthesis of PTD-MTX

PTD-MTX was synthesized through a solid phase synthesis method. For use as the peptide PTD, peptides of SEQ ID NO: 1 (Tyr Ala Arg Val Arg Arg Gly Pro Arg Arg) or SEQ ID NO: 2 (Ala Lys Ala Ala Arg Gln Ala Ala Arg) were prepared and used in tests. Amino acid residues that can cause side reactions during the synthesis reaction were protected before the PTD synthesis. Since side chains, such as A (alanine), V (valine), G (glycine) and P (proline), have no reactivity, a product was protected with Fmoc (fluorenylmethoxy carbonyl) only at $NH_2$, and since R (arginine), Y (tyrosine) and K (lysine) have no side-chain reactivity, they were protected with Pmc (2,2,5,7,8-pentamethylchroman-6-sulfonyl) and tBU (t-butyl), respectively. As in the above products, $NH_2$ was protected with Fmoc (fluorenylmethoxy carbonyl). 0.1 mmol MBHA resin (obtained from Beadtech; cat. No. SHI-B16) was swollen in DMF (dimethylformamide) for 15 minutes and treated two times with a mixed solution of piperidine and DMF (50:50) for 15 minutes to remove Fmoc. Meanwhile, 0.15 mmol of protected amino acids were mixed with 0.15 mmol of DIC (1,3-diisopropyl-cabodiimide) and 0.15 mmol of HOBt (N-hydroxybenzotriazole) in DMF solution, and the mixture was activated for 30 minutes and then mixed with the MBHA resin from which Fmoc was removed. Then, the mixture was allowed to react for about 4 hours and the above procedure was repeated three times. The reaction was repeated to synthesize a peptide of PTD-resin. Next, MTX (0.15 mmol) was mixed with 0.15 mmol PyBOP (benzotriazole-1-yl-oxy-tris-pyrrolidino-phosphoniumhexafluorophosphate) and 0.15 mmol HOBt (N-hydroxybenzotriazole) in DMF solution, and the mixture was activated for 30 minutes and mixed with the above PTD-resin, followed by reaction for 4 hours. Finally, the reaction product was allowed to react with a solution of TFA:$H_2$O:EDT:thioanisole:phenol = 8.25:0.5:0.25:0.25:0.75 for 24 hours so as to remove the respective amino acid-protecting groups and the resin. The resulting material was isolated and purified by HPLC and its weight measured. Then, the MTX-PTD conjugate isolated and purified by HPLC was lyophilized, thus obtaining the desired product.

Figure 4:
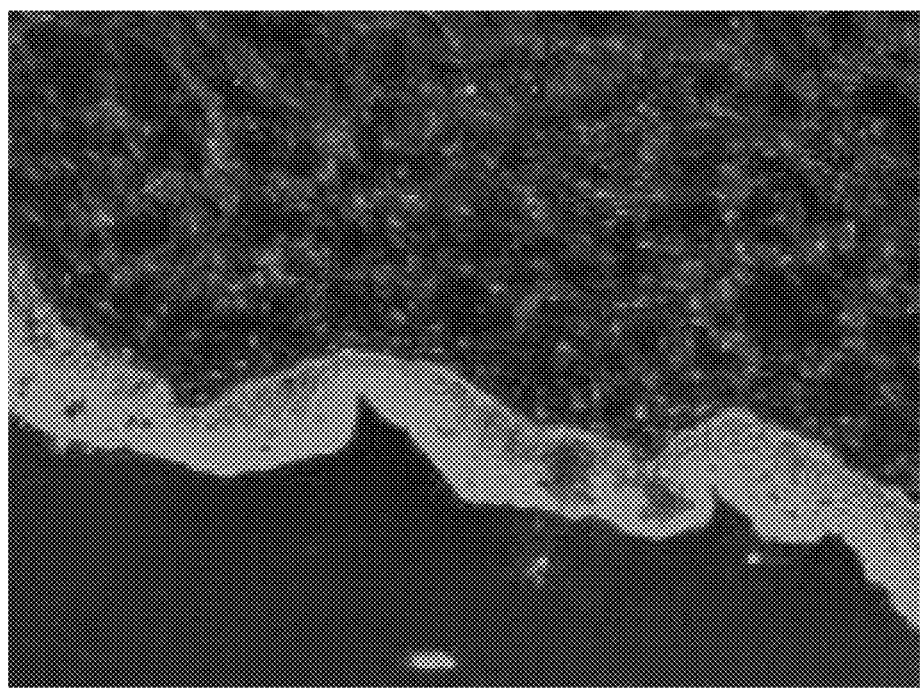
Figure 5:
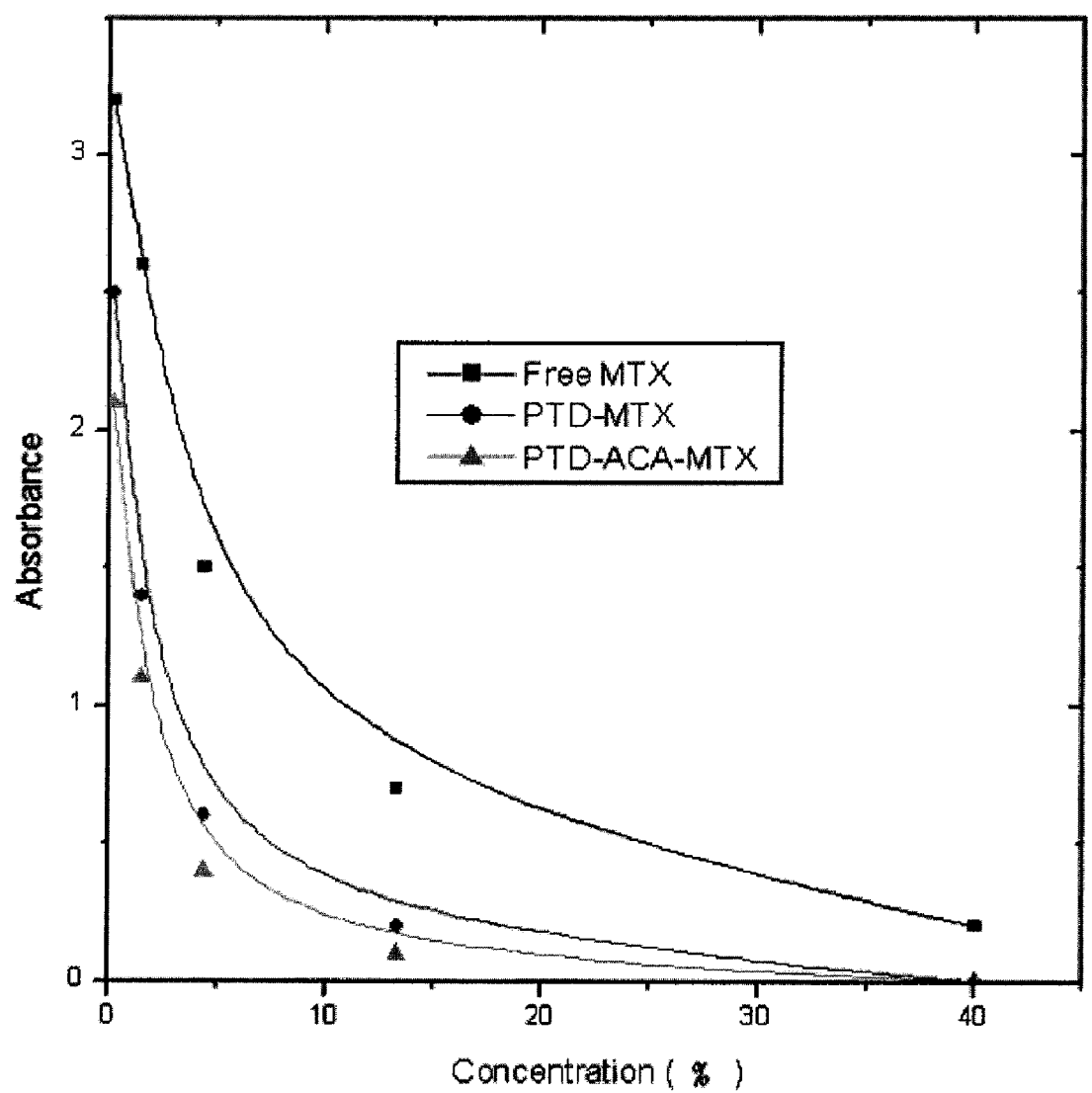
FIG. 5 is a graphic diagram showing the cell proliferation-inhibitory effect of the MTX-PTD conjugate according to the present invention.

Meanwhile, the peptide PTD has an α-helix structure. Therefore, when it is fused with MTX, MTX is unlikely to show effects due to steric hindrance effects caused by the three-dimensional structure of the peptide. For this reason, the present inventors solved this problem by introducing a linear linker capable of maintaining the structural distance between PTD and MTX. A linker used in the present invention was amino caproic acid (ACA). In solid phase synthesis, ACA-PTD-resin was synthesized in the same manner as above and was treated in the same manner as the above synthesis of the PTD-MTX conjugate, thus synthesizing a PTD-ACA-MTX conjugate (see FIGS. 4 and 5; only a conjugate prepared using PTD of SEQ ID NO: 1 is shown in the drawings).

Example 2

Transdermal Delivery Effects

To measure the transdermal delivery effect of PTD, PTD was chemically fused with fluorescent FITC, delivered to the skin and measured for the degree of its delivery. The PTD-FITC was prepared using amino caproic acid as a linker. As the skin to be delivered with the PTD-FITC, the skin of a 4-day-old pig having skin of an epidermal thickness similar to that of human skin was used. For use in the transdermal delivery test, an ointment formulation was prepared by mixing 10 mM PTD-FITC with a cream-type composition consisting of Vaseline:polyethylene glycol (8:2).

The back of the 4-day-old pig was shaved with a common razor, and the ointment formulation was applied evenly on a portion of the shaved back over an area of about 5 cm. After 2 hours, the pig was sacrificed and the skin was removed, freeze-sectioned and then observed with a confocal microscope to analyze the transdermal delivery efficiency of PTD. The observation results showed that PTD was delivered not only to the epidermis, but also to the dermis. This suggests the possibility of transdermal drug delivery (see FIG. 5; PTD of SEQ ID NO: 2 is not shown in the drawing).

Example 3

Effect of PTD-MTX In Vitro

In this Example, the cell proliferation-inhibitory effect of PTD-MTX was observed by WST-1 assay (Roche Biochemical) in vitro.

To analyze the cell proliferation-inhibitory effect of PTD-MTX, a HeCaT cell line (obtained from the Department of Dermatology, College of Medicine, Chungnam National University, Korea) was used to analyze cell death. For this purpose, $1 \times 10^6$ cells/well were inoculated into DMEM medium (10% FCS, antibiotics (GIBCO)) on a 96-well plate and cultured overnight. To the culture medium, MTX alone, PTD-MTX and PTD-ACA-MTX conjugates prepared in Example 1 were added with concentrations of 0.2, 1.5, 4.4, 13.3 and 40 µM respectively. After 2 days, the inhibition of proliferation of the cells was analyzed by the WST-1 assay.

In the WST-1 assay, tetrazolium salt is present in the respiratory chain of mitochondria and cleaved into a formazan dye by succinate-tetrazolium-reductase having activity only for viable cells, and if the number of viable cells increases, the entire activity of mitochondria dehydrogenase in a sample will increase. Since this increase in enzymatic activity induces an increase in the production of formazan dye, the formazan dye will show a linear correlation with the number of metabolically active cells in medium. The absorbance of the dye solution was measured with an ELISA reader to quantify the formazan dye produced by the metabolically active cells so as to observe cell proliferation ability and cell viability.

Figure 6:
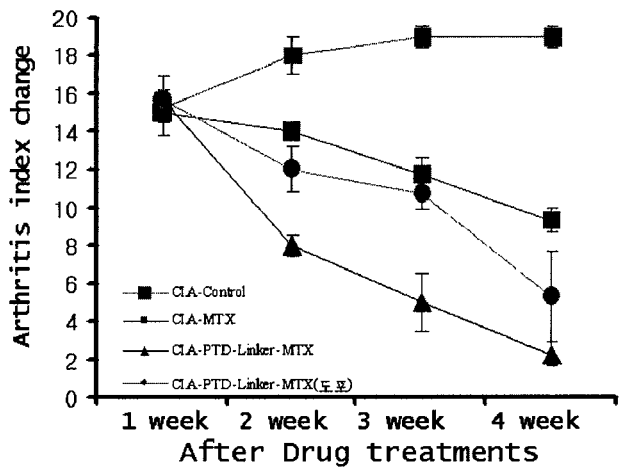
FIG. 6 is a graphic diagram showing a change in arthritis index caused by treatment with the MTX-PTD conjugate according to the present invention.

The test results showed that the cell proliferation-inhibitory effect was in the order of MTX alone <PTD-MTX<PTD-ACA-MTX. These results contrary to the prior enzyme test results that the PTD-MTX conjugate shows low effects compared to MTX alone are believed to be because: i) the intracellular delivery effect of MTD is promoted by PTD; and ii) the steric hindrance effect of PTD is removed by the intracellular metabolism of PTD. Also, it is believed that, since the MTX-PTD conjugate prepared in the present invention conserves the active site of MTX, the steric hindrance effect of PTD is disregarded (see FIG. 6; PTD of SEQ ID NO: 2 is not shown in the drawing).

Example 4

Effect of PTD-ACA-MTX in Arthritis Animal Model

Figure 7:
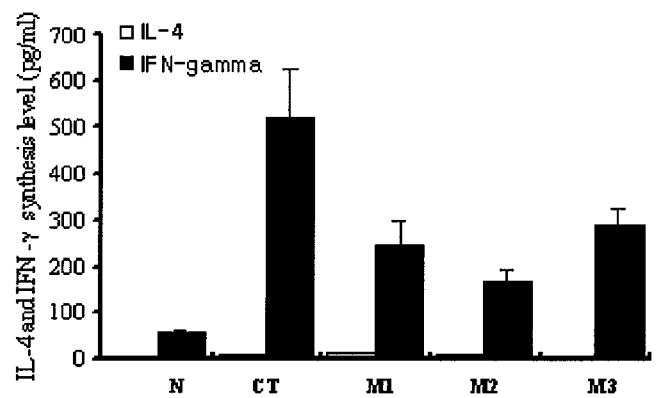
FIG. 7 is a graphic diagram showing the levels of IL-4 and IFN-γ in blood after treatment with the MTX-PTD conjugate according to the present invention.
Figure 8:
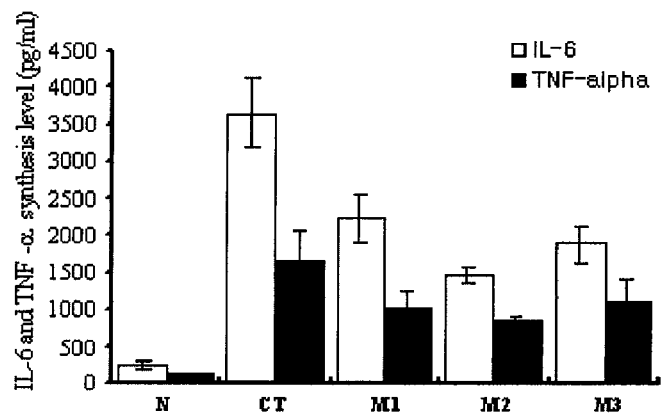
FIG. 8 is a graphic diagram showing the levels of IL-6 and TNF-β in blood after treatment with the MTX-PTD conjugate according to the present invention.
Figure 9:
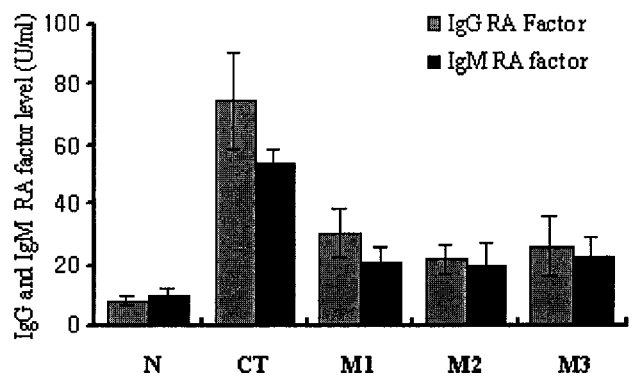
FIG. 9 is a graphic diagram showing the levels of RA factors in blood after treatment with the MTX-PTD conjugate according to the present invention.
Figure 10:
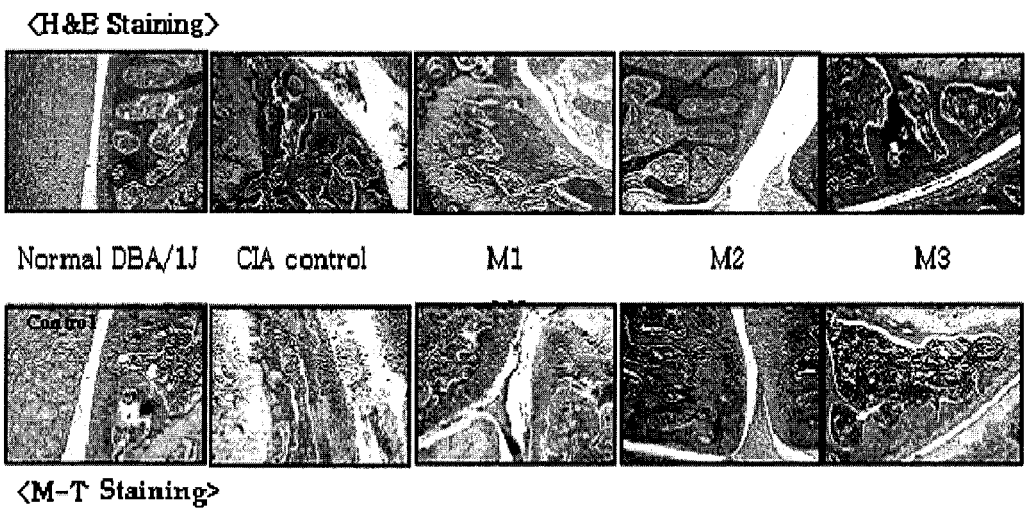
FIG. 10 is a photograph showing inflammatory tissues after treatment with the MTX-PTD conjugate according to the present invention.

For in vivo verification of the pharmacological effects of the PTD-ACA-MTX conjugate, DBA/1J mice (obtained from Samtako) were injected with e II-type collagen (obtained from Sigma) to induce rheumatoid arthritis. The mice were divided into a group for intraperitoneal (I.P.) injection of the PTD-ACA-MTX conjugate prepared in Example 1, a group for transdermal administration of the PTD-ACA-MTX conjugate prepared in Example 1, and a group for intraperitoneal (I.P.) injection of MTX alone. For the groups for intraperitoneal (I.P.) injection, MTX was injected in a dosage of 0.3 mg/kg for 4 weeks, and for the group for transdermal administration, a cream-type composition consisting of 5 wt %, based on the weight of the composition, of ethanol, 15 wt % of liquid paraffin, 40 wt % of Vaseline, 0.1 wt % of the PTD-ACA-MTX conjugate, 10 wt % of glycerin and 30 wt % of polyethylene glycol was prepared and then applied on rheumatoid arthritis-induced sites four times weekly. After treatment with the drugs, the arthritis index was monitored one time each week, and after 4 weeks, the animals were sacrificed and the IL-4, IL-6, TNF-α and arthritis factor levels in the blood were measured (see FIGS. 7, 8 and 9; results obtained using PTD of SEQ ID NO: 2 are not shown in the drawings). In FIGS. 7, 8 and 9, N: normal mice; CT: mice having rheumatoid arthritis induced by injection of collagen; M1: the group injected intraperitoneally with MTX alone; M2: the group injected intraperitoneally with PTD-ACA-MTX; and M3: the group for which the ointment preparation containing the PTD-ACA-MTX conjugate was administered transdermally.

As a result, it was observed that the amount of inflammation-mediating cytokine, such as TNF-α, which is most important in rheumatoid arthritis, was greatly decreased. Also, it was confirmed in tissue photographs that inflammatory cells, which have penetrated inflammatory sites, were greatly decreased as a result of treatment with the drug. This suggests that the PTD-ACA-MTX conjugate permeated the skin to effectively inhibit the activities of various inflammatory cells and immune cells (see FIG. 8; results obtained using PTD of SEQ ID NO: 2 are not shown in the drawing). In FIG. 8, the upper photographs show the results of H&E staining, the lower photographs show the results of M-T staining, Normal DBA/1J represents a normal DBA/1J mouse obtained from Samtako, CIA control represents a mouse having rheumatoid arthritis induced by injecting e II-type collagen, M1 represents the group injected intraperitoneally with MTX alone, M2 represents the group injected intraperitoneally with PTD-ACA-MTX, and M3 represents the group for which the ointment preparation containing PTD-ACA-MTX was administered transdermally.

Example 5

Effect of PTD-ACA-MTX in Inflammatory Disease Model

Figure 11:
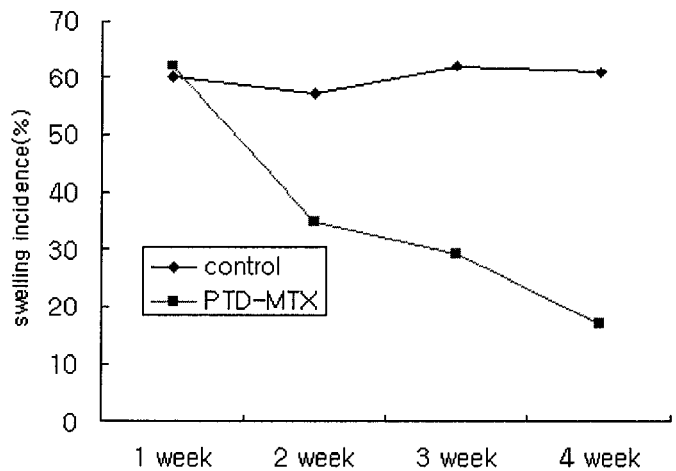
FIG. 11 is a graphic diagram showing the swelling inhibitory effect of the MTX-PTD conjugate in an animal model having TPA-induced inflammation.

To confirm therapeutic effects against psoriasis, the PTD-ACA-MTX conjugate prepared in Example 1 was analyzed for its therapeutic effect against skin inflammation. TPA (12-O-tetradecanoylphorbol-13-acetate; Alexis biochemical, San Diego) was applied to the ear of an ICR mouse (obtained from Samtako) once a day for 3 days to induce skin inflammation. 5 days after the start of the experiment, the thickness of the ear was measured with a micrometer screw, and the swollen thickness was calculated and used as an index of chronic edema. Also, the ear was punched and inflammatory cells in the inflammatory site were analyzed. A composition for transdermal delivery containing the PTD-ACA-MTX conjugate was applied to the ear skin. The composition was prepared in the same manner as in the example described above, and applied once a day for 10 days (see FIG. 11).

Example 6

Toxicity Test by Single Subcutaneous Administration to Rats

Toxicity by the single subcutaneous administration of PTD-ACA-MTX prepared in Example 1 was examined. Male and female Sprague Dawley rats (Samtako) were divided into an excipient control group administered with sterilized water for injection, and test groups administered with the inventive conjugate in amounts of 5, 50 and 500 mg/kg. Each of the animal groups consisted of 10 animals (five males and five females) and observed for mortality for 2 weeks, general symptoms, bodyweight change, and autopsy findings. All the test methods were performed according to toxicity test standards provided by the Korea Food and Drug Administration, and the test results are as follows.

i) Animals being killed by the test substance were not observed throughout the test period.

ii) In the male and female animals of the group administered with 500 mg/kg of the test substance, congestion was observed starting from one day after the administration, and incrustation was observed starting from 2 days after the administration. In the male animals of the group administered with 500 mg/kg of the test substance, even systemic edema was observed. Diarrhea and soft feces were sporadically observed during a period ranging from 4 days to 6 days after the administration.

iii) Regarding bodyweight change, in the male animals of the group administered with 500 mg/kg of the test substance, the inhibition of an increase in bodyweight, caused by the test substance, was observed at 3 days, 7 days and 14 days after administration.

iv) Regarding autopsy findings, in the male and female animals of the group administered with 500 mg/kg of the test substance, red fluid retention and incrustation caused by the test material were observed at the administration site. In the female animals, splenomegaly was observed.

From the above results, it was estimated that subcutaneous administration of the inventive conjugate to rats in the above test conditions would show a minimum lethal dose (MLD) of more than 500 mg/kg in the case of the group administered with 500 mg/kg of the test substance.

Example 7

Toxicity Test by Single Subcutaneous Administration to Beagle Dogs

Toxicity caused by single subcutaneous administration of the inventive conjugate was examined. Male and female beagle dogs were administered subcutaneously with the inventive conjugate in each of amounts of 4, 20 and 100 mg/kg. Each of the animal groups consisted of four animals (2 males and 2 females) and observed for mortality for 2 weeks, general symptoms, bodyweight change, and autopsy findings. All the test methods were performed according to toxicity test standards provided by the Korea Food and Drug Administration, and the test results are as follows.

i) No animal killed by the test substance was observed throughout the test period.

ii) In the males and females of all the groups administered with more than 20 mg/kg of the conjugate, eyelid edema was observed during a period ranging from 1 hour to 6 hours after administration of the test substance. In one male and female of the group administered with 100 mg/kg of the test substance, a reduction in spontaneous motility was observed starting from 1 hour after administration. In one male of the group administered with 20 mg/kg of the test substance and one female of the group administered with 100 mg/kg of the test substance, edema and a reduction in spontaneous motility were continued up to 2 days after administration. In the males of the group administered with 100 mg/kg of the test substance, anorexia was observed during a period ranging from 2 days to 4 days after administration, and diarrhea was observed 3 days after administration.

iii) Regarding bodyweight change, in the male and female animals of the group administered with 100 mg/kg of the test substance, temporary inhibition of an increase in bodyweight, caused by the test substance, was observed 3 days after administration.

iv) Regarding autopsy, abnormal findings were not observed.

In summary, the results of subcutaneous administration of the inventive conjugate to beagle dogs in the above test conditions were as follows: the males and females of the groups administered with more than 20 mg/kg of the test substance showed eyelid edema; the male of the group administered with 100 mg/kg showed a reduction in spontaneous motility, temporary anorexia and diarrhea; and the group administered with 100 mg/kg showed a spontaneous reduction in bodyweight at 3 days after the administration. From the above results, it was estimated that the minimum lethal dose by subcutaneous administration of the inventive conjugate would be over 100 mg/kg for both males and females.

Example 8

Skin Irritation Test in Rabbits

The skin irritability of the inventive conjugate was examined. The inventive conjugate was applied to the healthy skin and scratch skin of New Zealand White rabbits, which were then evaluated comparatively with the healthy skin and scratch skin to which the inventive conjugate had not been applied. The results are as follows.

i) Abnormal general symptoms by the application of the test substance were not observed.

ii) An abnormal change in bodyweight caused by the application of the test substance was not observed.

iii) Any abnormality in the normal and scratch sites was not observed throughout the observation period after the application of the test substance.

iv) The evaluation result of skin irritability showed that the skin irritation index of the test substance was zero, indicating that the test substance is a non-irritating substance. The skin irritation index of the control substance was 0.17, indicating that it is a non-irritating substance.

In summary, the results of the skin irritation test conducted on New Zealand White rabbits in the above test conditions indicate that the inventive conjugate is a non-irritating substance.

INDUSTRIAL APPLICABILITY

As described above, the inventive pharmaceutical composition for transdermal delivery containing the methotrexate-PTD conjugate can be applied to the skin in a simple manner, such that it can effectively deliver methotrexate while minimizing side effects.

What is claimed is:

1. A method for transdermally delivering methotrexate for the treatment of autoimmune disease, the method comprising applying to the skin of a patient in need thereof a transdermal pharmaceutical composition comprising 0.01-0.5 wt % of a conjugate of methotrexate and PTD (protein transduction domain), wherein the PTD is selected from the amino acid sequence SEQ ID No: 1 or SEQ ID No: 2.

2. The method of claim 1, wherein the PTD and the methotrexate are linked to each other by a direct covalent bond, a peptide bond, or a linker.

3. The method of claim 2, wherein the linker comprises an —O— or —S—S— bond.

4. The method of claim 3, wherein the linker is amino caproic acid.

5. The method of claim 1, wherein the autoimmune disease is psoriasis or rheumatoid arthritis.

* * * * *